United States Patent [19]

Mues et al.

[11] 4,288,451

[45] Sep. 8, 1981

[54] COMBATING ARTHROPODS WITH FERROCENE-CONTAINING SYNERGISTIC COMPOSITIONS

[75] Inventors: Volker Mues, Wuppertal; Wolfgang Behrenz, Overath, both of Fed. Rep. of Germany

[73] Assignee: Bayer Aktiengesellschaft, Leverkusen, Fed. Rep. of Germany

[21] Appl. No.: 53,563

[22] Filed: Jun. 29, 1979

Related U.S. Application Data

[62] Division of Ser. No. 882,824, Mar. 2, 1978, Pat. No. 4,206,227.

[30] Foreign Application Priority Data

Mar. 17, 1977 [DE] Fed. Rep. of Germany ....... 2711546

[51] Int. Cl.$^3$ .................. A01N 37/00; A01N 37/34; A01N 43/02; A01N 43/08; A01N 43/36; A01N 55/02; A01N 57/00; A01N 65/00

[52] U.S. Cl. .................. 424/295; 424/186; 424/189; 424/190; 424/192; 424/193; 424/198; 424/199; 424/200; 424/203; 424/204; 424/210; 424/211; 424/212; 424/214; 424/215; 424/216; 424/217; 424/218; 424/219; 424/220; 424/225; 424/274; 424/278; 424/285; 424/304; 424/305; 424/308; 424/309; 424/311; 424/312; 424/314

[58] Field of Search .............. 424/295, 304, 305, 308, 424/309, 310, 285, 311, 312, 314, 186, 274, 278, 198, 199, 200, 204, 210, 211, 212, 214, 215, 203, 216, 217, 218, 219, 220, 225

[56] References Cited

U.S. PATENT DOCUMENTS

| | | | |
|---|---|---|---|
| 3,035,978 | 5/1962 | Jones et al. ................ | 424/295 |
| 3,432,533 | 3/1969 | Rosenberg .................. | 260/439 |
| 3,511,858 | 5/1970 | Bublitz ...................... | 260/349 |
| 3,553,241 | 1/1971 | Suh et al. .................. | 260/439 |
| 3,557,143 | 1/1971 | Suh et al. .................. | 260/327 |
| 3,558,780 | 1/1971 | Bublitz ...................... | 424/295 |
| 3,960,911 | 6/1976 | Suschitzky et al. ......... | 424/295 |
| 3,966,783 | 6/1976 | Suschitzky et al. ......... | 424/295 |
| 3,984,567 | 10/1976 | Nikolaevich et al. ....... | 424/295 |
| 4,036,983 | 7/1977 | Rutherford et al. ......... | 424/295 |
| 4,038,413 | 7/1977 | Suschitzky et al. ......... | 424/295 |

FOREIGN PATENT DOCUMENTS

898633 7/1962 United Kingdom .

OTHER PUBLICATIONS

Nesmeyanov et al., C. A. vol. 80, (1974), 48165m.

*Primary Examiner*—Allen J. Robinson
*Attorney, Agent, or Firm*—Sprung, Felfe, Horn, Lynch & Kramer

[57] ABSTRACT

An arthropodicidal composition containing, as active ingredients, an arthropodicidally effective amount of (1) at least one ferrocene derivative of the formula in which R and $R^1$ each independently is hydrogen, an alkyl or alkenyl radical optionally substituted by alkoxycarbonyl, aralkyl, cyanoalkyl, nitrile, or $$-\underset{X}{\overset{\|}{C}}-R^2, \quad -\underset{OR^3}{\overset{|}{CH}}-R^2 \text{ or } \begin{array}{c} YR^4 \\ | \\ -C-R^2 \\ | \\ YR^5 \end{array}$$

$R^2$ is hydrogen, optionally substituted alkyl, optionally substituted cycloalkyl, optionally substituted phenyl or alkoxy, $R^3$ is hydrogen, alkyl, alkanoyl or a polyalkylene polyether group, $R^4$ and $R^5$ each independently is alkyl or together are an alkylene radical, X is oxygen, hydroxyimino or alkoxyimino and, Y is oxygen or sulphur, and (2) at least one compound selected from (A) carbamates, (B) carboxylic acid esters, including the natural and synthetic pyrethroids, (C) phosphoric acid esters, (D) cycloalkanes, (E) halogenoalkanes and (F) tin compounds.

10 Claims, No Drawings

COMBATING ARTHROPODS WITH FERROCENE-CONTAINING SYNERGISTIC COMPOSITIONS

This is a division of Application Ser. No. 882,824, filed Mar. 2, 1978, now U.S. Pat. No. 4,206,227.

The present invention relates to new arthropodicidal (especially insecticidal and acaricidal) synergistic combinations of certain ferrocene derivatives, some of which are known, and certain other pesticidal active compounds.

It has already been disclosed that ferrocene derivatives can be used for the treatment of iron deficiency anaemias in humans and animals and as antioxidants, antiknock agents, fuel and oil additives, organic pigments, radiation absorbers, insecticides and fungicides (see British Patent Specification No. 898,633, U.S. Pat. Nos. 3,432,533, 3,535,536, 3,553,241, 3,557,143, 3,511,858 and 3,558,780, German Offenlegungsschriften (German Published Specifications) 2,107,657, 2,453,936 and 2,453,977 and U.S.S.R. Patent Specification No. 400,597).

Furthermore, it is already known that the following active compounds and groups of active compounds have pesticidal, in particular insecticidal and acaricidal, properties:

(A) carbamates, for example 2-iso-propoxy-phenyl N-methyl-carbamate, 3,4,5-trimethyl-phenyl-N-methyl-carbamate, 1-naphthyl N-methyl-carbamate, 2,3-dihydro-2,2,-dimethyl-7-benzofuranyl N-methyl-carbamate, 2-[1,3-dioxolan-2-yl-phenyl] N-methyl-carbamate and 2,2-dimethyl-1,3-benzodioxol-4-yl N-methyl-carbamate;

(B) carboxylic acid esters, for example 2,3,4,5-tetrahydrophthalimidomethyl chrysanthemate and (5-benzoyl-3-furyl)-methyl 2,2-dimethyl-3-(2-methylpropenyl)-cyclopropane-carboxylate;

(C) phosphoric acid esters, for example O,O-dimethyl-O-(2,2-dichlorovinyl)-phosphoric acid ester;

(D) cycloalkanes, for example hexachlorocyclohexane;

(E) halogenoalkanes, for example 1,1,1-trichloro-2,2-bis-(4-methoxyphenyl)-ethane; and (F) tin compounds.

Furthermore, synergistic mixtures of carbamates, for example 2-iso-propoxy-phenyl N-methylcarbamate, or of phosphoric acid esters, for example O,O-diethyl-O-[2-iso-propyl-4-methyl-pyrimidin-6-yl]-thionophosphoric acid ester, or of natural or synthetic pyrethroids with piperonyl ethers, for example α-[2-(2-butoxy-ethoxy)-ethoxy]-4,5-methylenedioxy-2-propyl-toluene, are known (see Bull. Org. Health Org. 1966, 35, pages 691–708; Schrader, G., Die Entwicklung neuer insektizider Phosphorsäureester (The development of new insecticidal phosphoric acid esters) 1963, page 158; and Perkov, W., Die Insektizide (Insecticides), 1966, pages 516–524). However, the activity of these synergistic active compound combinations is not satisfactory. Only α-[2-(2-butoxy-ethoxy)-ethoxy]-4,5-methylenedioxy-2-propyl-toluene has hitherto acquired a certain practical importance.

The present invention now provides an arthropodicidal composition containing as active ingredients (1) at least one ferrocene derivative of the general formula

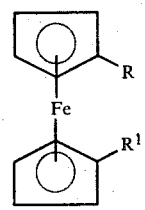

in which

R and R¹, which can be identical or different, each represent hydrogen, alkyl or alkenyl (either of which is optionally substituted by alkoxycarbonyl), aralkyl, cycanoalkyl, nitrile or a radical

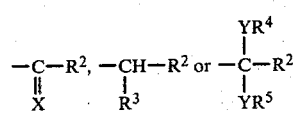

wherein

R² represents hydrogen, optionally substituted alkyl, optionally substituted cycloalkyl, optionally substituted phenyl or alkoxy, R³ represents hydrogen, alkyl, alkanoyl or a polyalkylene polyether group, R⁴ and R⁵ each represent alkyl or together represent an alkylene radical, X represents oxygen, hydroxyimino or alkoxyimino and Y represents oxygen or sulpher.

and (2) at least one compound selected from (A) carbamates, (B) carboxylic acid esters, including the natural and synthetic pyrethroids, (C) phosphoric acid esters (D) cycloalkanes (E) halogenoalkanes and (F) tin compounds, alone or in admixture with a solid or liquid or liquefied gaseous diluent or carrier.

The invention also provides a method of combating arthropods, especially insects or acarids, which comprises applying to the arthropods, or to a habitat thereof, a composition according to the present invention.

Surprisingly, the insecticidal and/or acaricidal action of the active compound combinations according to the invention is substantially higher than the action of the individual components or the sum of the actions of the individual components. Furthermore, it is substantially higher than the action of the known active compound combination consisting of 2-isopropoxy-phenyl N-methylcarbamate and piperonyl butoxide. In addition, the ferrocene derivatives which can be used according to the invention exhibit an excellent synergistic activity not only with one class of active compounds but with active compounds from the most diverse chemical groups of substances.

The synergistic mixtures according to the invention containing ferrocene derivatives thus represent a valuable enrichment of the art.

The preferred ferrocene derivatives of the formula (I) are those
in which
R and R¹ each represent hydrogen, straight-chain or branched alkyl or alkenyl with up to 20 carbon atoms, straight-chain or branched alkyl or alkenyl with up to 10 carbon atoms, which is substituted by carbalkoxy with up to 4 carbon atoms per alkoxy, benzyl, nitrile, cyanomethyl, cyanoethyl,

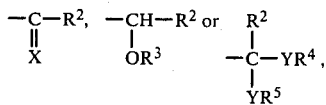

R² represents hydrogen, straight-chain or branched alkoxy with 1 to 10 carbon atoms, straight-chain or branched alkyl with 1 to 19 carbons atoms, cycloalkyl with 3 to 12 carbon atoms or phenyl, it being possible for the alkyl, cycloalkyl or phenyl optionally to carry one or more substituents selected independently from halogen, alkyl, hydroxyl, halogencalkyl, nitro, nitrile and alkoxy, R³ represents hydrogen or straight-chain or branched alkyl with 1 to 8 carbon atoms, R⁴ and R⁵ each represent straight-chain or branched alkyl with 1 to 6 carbon atoms or together represent an alkylene radical with 1 to 6 carbon atoms, X represents oxygen, hydroxyimino or straight-chain or branched alkoxyimino with 1 to 6 carbon atoms, and Y represents oxygen or sulphur.

The preferred carbamates (A) are those of the general formula

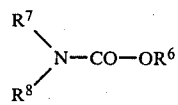

in which
R⁶ represents aryl, a heterocyclic radical or an oxime radical,
R⁷ represents hydrogen or alkyl with 1 to 4 carbon atoms and
R⁸ represents alkyl, alkylcarbonyl with 1 to 6 carbon atoms in the alkyl radical, which can optionally be substituted by hydroxyl or methylthio, or the radical —S—Z,
wherein
Z represents an aliphatic radical with 1 to 4 carbon atoms which is optionally substituted by halogen (especially CCl₃ and CF₃) or represents an aryl radical (especially phenyl) which is optionally substituted (preferably by nitrile, halogen (especially chlorine), methyl, trihalogenomethyl, trifluoromethylmercapto or nitro), methoxycarbonyl or the radical

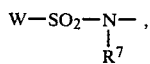

wherein
W represents alkyl, halogenoalkyl, alkylamino, dialkylamino or an aryl radical which is optionally substituted (preferably by halogen, trihalogenomethyl, nitrile, methyl or nitro).

Particularly preferred carbamates of the formula (II) are those
in which
R⁶ represents phenyl or naphthyl, either of which is optionally substituted by alkyl, alkenyl, alkoxy, alkylmercapto or alkylthioalkylene with 1 to 5 carbon atoms in each case, dialkylamino or dialkenylamino with up to 3 carbon atoms per alkyl or alkenyl part respectively, halogen (especially chlorine), dioxolanyl or the radical —N=CH—N(C₁₋₄-alkyl)₂. Furthermore, carbamates of the formula (II)
in which
R⁶ represents 2,3-dihydrobenzofuranyl, benzodioxolyl, benzothienyl, pyrimidinyl or pyrazolyl, any one of which is optionally substituted by C₁₋₄-alkyl (especially methyl) or dialkylamino with 1 to 4 carbon atoms per alkyl part, or
in which
R⁶ represents an oxime radical of the general formula

in which
R⁹ and R¹⁰, which may be identical or different, each represent alkyl, cycloalkyl, alkenyl, alkynyl, alkoxy, alkylmercapto, alkoxycarbonyl, carbonylamide or alkylmercaptoalkyl with up to 5 carbon atoms in each case, nitrile, aryl (especially phenyl), an optionally substituted heterocyclic radical or alkyl which is substituted by a heterocyclic radical, or R⁹ and R¹⁰ together complete a dioxolanyl or dithiolanyl radical which is optionally substituted by C₁₋₄-alkyl, are also particularly preferred.

Preferred carboxylic acid esters (B) are those of the general formula

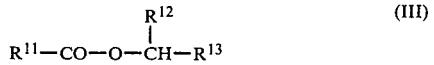

in which
R¹¹ represents alkyl, aralkyl, aryl or cycloalkyl, any one of which can be optionally substituted,
R¹² represents hydrogen, alkyl, halogenoalkyl, alkenyl, alkynyl or nitrile and
R¹³ represents aryl or a heterocyclic radical or, together with R¹², forms an optionally substituted cyclopentenone ring.

Particularly preferred carboxylic acid esters of the formula (III) are those
in which
R¹¹ represents alkyl with 1 to 6 carbon atoms (which is optionally substituted by optionally halogen-substituted phenyl), cyclopropyl (which is optionally substituted by alkyl, alkenyl, halogenoalkyl or halogenoalkenyl with up to 6 carbon atoms in each case) or phenyl (which is optionally substituted by halogen), and/or
in which
R¹² represents hydrogen, alkyl with 1 to 6 carbon atoms, halogenoalkyl with 1 to 4 carbon atoms and up to 3 halogen atoms, nitrile or ethynyl, and/or
in which
R¹³ represents phenyl which is optionally substituted by C₁₋₄-alkyl, halogen (especially fluorine or chlorine), optionally halogen-substituted or methyl-substituted phenoxy or optionally substituted benzyl, or represents furanyl, tetrahydrophthalimido or benzodioxolyl, and one of which is optionally substituted by halogen (especially chlorine), alkyl or alkenyl each with up to 4 carbon atoms or benzyl, or represents cyclopentenone which is optionally substituted by $C_{1-4}$—alkyl, furfuryl or $C_{1-5}$—alkenyl.

The naturally occurring pyrethroids are also particularly preferred.

Preferred phosphoric acid esters (C) are those of the general formula

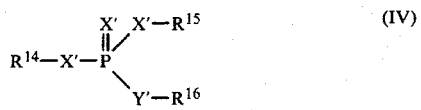

in which
  each X', independently of the other, represents O or S,
  Y' represents, O, S, —NH— or a direct bond between the central P atom and the radical $R^{16}$,
  $R^{14}$ and $R^{15}$, which may be identical or different, each represent alkyl or aryl and
  $R^{16}$ represents alkyl, aryl, hetero-aryl, aralkyl, alkenyl, dioxanyl or an oxime radical, or represents a radical idential to that to which it is bonded.

Particularly preferred phosphoric acid esters of the formula (IV) are those
in which
  $R^{14}$ and $R^{15}$, which may be identical or different, each represents $C_{1-4}$—alkyl or phenyl and
  $R^{16}$ represents alkyl with 1 to 4 carbon atoms which is optionally substituted by halogen, hydroxyl, nitrile, optionally halogen-substituted phenyl, carbonylamide, sulphonylalkyl, sulphoxyalkyl, carbonylalkyl, alkoxy, alkylmercapto or alkoxycarbonyl, or represents alkenyl with up to 4 carbon atoms which is optionally substituted by halogen, optionally halogen-substituted phenyl or alkoxycarbonyl, or represents the oxime radical of the general formula

wherein
  $R^9$ and $R^{10}$ have the meanings stated above (especially cyano or phenyl), or
  $R^{16}$ represents dioxanyl which is substituted by a radical identical to that to which $R^{16}$ is bonded, or
  $R^{16}$ represents a radical identical to that to which it is bonded, or
  $R^{16}$ represents phenyl which is optionally substituted by methyl, nitro, nitrile, halogen or methylthio, or
  $R^{16}$ represents a hetero-aromatic radical (such as pyridine, quinoline, quinoxaline, pyrimidine, diazinone or benzo-1,2,4-triazine) which is optionally substituted by $C_{1-4}$—alkyl or halogen.

Preferred cycloalkanes (D) are those of the general formula

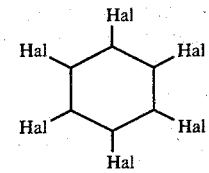

in which
  Hal denotes halogen, preferably chlorine.

Preferred halogenoalkanes (E) are those of the general formula

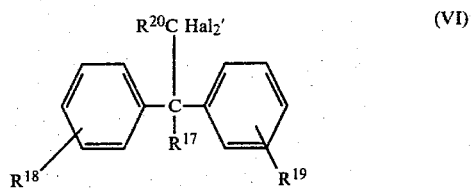

in which
  Hal' represents chlorine or bromine,
  $R^{17}$ represents hydrogen or hydroxyl,
  $R^{18}$ and $R^{19}$, which may be identical or different, each represent halogen, alkyl or alkoxy and
  $R^{20}$ represents hydrogen or halogen.

Particularly preferred halogenoalkanes of the formula (VI) are those
in which
  $R^{17}$ denotes hydrogen or hydroxyl,
  $R^{18}$ and $R^{19}$ are identical and represent halogen or alkyl or alkoxy each with 1 to 4 carbon atoms, and
  $R^{20}$ denotes halogen.

Preferred tin compounds (F) are those of the general formula $$(Cycloalk)_3Sn-X'' \qquad (VII),$$

in which
  Cycloalk represents cycloalkyl with 5 to 8 carbon atoms and
  X'' represents hydrogen, halogen, hydroxyl, alkoxycarbonyl, a heterocyclic radical or a radical identical to that to which X'' is bonded.

Particularly preferred tin compounds of the formula (VII) are those
in which
  Cycloalk represents cyclohexyl and
  X'' represents 1,2,4-triazole, hydroxyl or halogen.

Examples of ferrocene derivatives of the formula (I) which can be used according to the invention are: ferrocene, methylferrocene, ethylferrocene, n-propylferrocene, isopropylferrocene, n-butylferrocene, isobutylferrocene, tert.-butylferrocene, n-pentylferrocene, iso-pentylferrocene, n-hexylferrocene, n-heptylferrocene, n-octylferrocene, n-nonylferrocene, n-decylferrocene, diethylferrocene, di-n-propylferrocene, di-n-butylferrocene, di-n-pentylferrocene, benzylferrocene, ferrocenecarboxylic acid nitrile, formylferrocene and its oxime O-methyl ether and oxime O-ethyl ether, acetylferrocene and its oxime O-methyl ether and oxime O-ethyl ether, propionyl ferrocene and its oxime O-methyl ether and oxime O-ethyl ether, n-butyroferrocene and its oxime O-methyl ether and oxime O-ethyl ether, benzoylferrocene and its oxime O-methyl ether and oxime O-ethyl ether, n-pentanoylferrocene, n-hexanoylferrocene, n-heptanoylferrocene, n-octanoylferrocene, n-nonanoylferrocene, n-decanoylferrocene, diacetylferrocene, dibenzoylferrocene, ferrocenecarbonitrile, ferrocene-carboxylic acid methyl ester, ferrocene-carboxylic acid ethyl ester, ferrocene-carboxylic acid n-propyl ester, ferrocene-carboxylic acid iso-propyl ester, ferrocene-carboxylic acid n-butyl ester, ferrocenecarboxylic acid iso-butyl ester, ferrocene-acrylic acid methyl ester, ferrocene-acrylic acid ethyl ester, ferrocene-hydracrylic acid methyl ester, ferrocene-hydracrylic acid ethyl ester, ferrocenylmethanol and its acetate, 1-ferrocenylethanol and its acetate, 1-ferrocenyl-n-propanol and its acetate, 1-ferrocenyl-n-butanol and its acetate, 1-ferrocenyl-n-pentanol, 2-ferrocenyldioxolane and 2-ferrocenylthioxolane.

Some of the ferrocene derivatives of the formula (I) which can be used according to the invention are known (see "Organic Reactions", volume 17, chapter 1, page 1 to 151). However, their use as synergistic agents for carbamates, carboxylic acid esters, phosphoric acid esters, cycloalkanes, halogenoalkanes or tin compounds is new.

Certain of the ferrocene derivatives which can be used according to the invention have not yet been described in the literature, but they can be prepared in a simple manner by processes which are known in principle.

The ferrocene derivatives of the formula (I) which can be used according to the invention are obtained, for example, when (a) ferrocene is reacted with an acyl chloride $R^2COCl$, in which $R^2$ has the meaning stated above, or with an acid anhydride

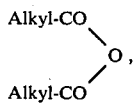

optionally in the presence of a solvent, for example methylene chloride, and in the presence of a Friedel-Crafts catalyst, for example aluminum chloride, zinc chloride, boron trifluoride, hydrogen fluoride or phosphoric acid, at temperatures between 0° and 100° C., or when (b) ferrocene-carboxylic acid is converted into the esters by customary methods, or when (c) a ferrocene-ketone derivative is reduced by customary methods.

The carbamates (group A) of the formula (II) include: 2-methylphenyl, 2-ethylphenyl, 2-n-propylphenyl, 2-methoxyphenyl, 2-ethoxyphenyl, 2-iso-propoxyphenyl, 4-methylphenyl, 4-ethylphenyl, 4-n-propylphenyl, 4-methoxyphenyl, 4-ethoxyphenyl, 4-n-propoxyphenyl, 3,4,5-trimethylphenyl, 1-naphthyl, 2,3-dihydro-2,2-dimethyl-7-benzofuranyl, 2-[1,3-dioxolan-2-yl-phenol] or 2,2-dimethyl-1,3-benzodioxo-4-yl N-methyl-carbamate and the corresponding N-methyl-N-acetyl-carbamates, N-methyl-N-trifluoromethylthiocarbamates, N-methyl-N-dichloromonofluoromethylthiocarbamates or N-methyl-N-dimethylaminothio-carbamates.

These compounds, their preparation and their use are known (see, for example, U.S. Pat. Nos. 3,009,855, 2,903,478 and 3,111,539).

Carboxylic acid esters (group B) of the formula (III) include: acetic acid 1-(3,4-dichlorophenyl)-2,2,2-trichloroethyl ester, 2,3,4,5-tetrahydrophthalimidomethyl chrysanthemate and (5-benzyl-3-furyl)-methyl-2,2-dimethyl-3-(2-methylpropenyl)-cyclopropanecarboxylate. The compounds listed are known and the majority are generally known commercial products [see R. Wegler "Chemie der Pflanzenschutz- und Schädlingsbekämpfungsmittel" ("Chemistry of Plant Protection Agents and Agents for Combating Pests"), volume 1; pages 87–118, Heidelberg (1970)].

Phosphoric acid esters (group C) of the formula (IV) include: O,O-dimethyl- or O,O-diethyl-O-(2,2-dichloro- or 2,2-dibromo-vinyl)-phosphoric acid ester, O,O-diethyl-O-(4-nitro-phenyl)-thionophosphoric acid ester, O,O-dimethyl-O-(3-methyl-4-methylthio)-thionophosphoric acid ester, O,O-dimethyl-O-(3-methyl-4-nitro)-thionophosphoric acid ester, O-ethyl-S-n-propyl-O-(2,4-dichlorophenyl)-thionophosphoric acid ester, O-ethyl-S-n-propyl-O-(4-methylthiophenyl)-thionophosphoric acid ester, O,O-dimethyl-S-[4-oxo-1,2,3-benzotriazin-3-yl-methyl]-thionothiolphosphoric acid ester, O-methyl-O-[2-iso-propyl-6-methoxy-pyrimidin-4-yl]-thionomethanephosphonic acid ester, O,O-diethyl-O-[2-isopropyl-6-methyl-pyrimidin-4-yl]-thionophosphoric acid ester, O,O-diethyl-O-[3-chloro-4-methyl-coumarin-7-yl]-thionophosphoric acid ester, O,O-dimethyl-2,2,2-trichloro-1-hydroxy-ethane-phosphonic acid ester and O,O-dimethyl-S-(methylcarbamoylmethyl)-thionophosphoric acid ester.

The compounds of the formula (IV) are known and are easily producible by processes which are known from the literature (see, for example, U.S. Pat. No. 2,956,073, German Auslegeschrift (German Published Specification) No. 1,167,324 and Belgian Patent Specification No. 633,478).

The cycloalkanes (group D) of the formula (IV) include: 1,2,3,4,5,6-hexachlorocyclohexane.

These compounds, their preparation and their use are known (see, for example, U.S. Pat. No. 2,502,258; and Chem+Industry 1945, page 314).

The halogenoalkanes (group E) of the formula (V) include: 1,1,1-trichloro-2,2-bis-(4-chloro- or 4-methoxyphenyl)-ethane, 1,1,1-trichloro-2-hydroxy-2,2,-bis-(4-chlorophenyl)-ethane and 1,1-dichloro-2,2-bis-(4-ethylphenyl)-ethane.

These compounds, their preparation and their use are known (see, for example, U.S. Pat. Nos. 2,420,928, 2,464,600, 2,883,428 and 2,917,553).

The tin compounds (group F) of the formula (VI) include: 1-tricyclohexyltin-1,2,4-triazole, tricyclohexyltin hydroxide and tricyclohexyltin chloride.

These compounds, their preparation and their use are known (see, for example, U.S. Pat. Nos. 3,264,177 and 3,355,470, British Patent Specification No. 1,082,904 and French Patent Specification No. 1,432,329).

The weight ratios of the groups of active compounds can vary within relatively wide ranges. In general, the ferrocene component (1) is employed in the weight ratio of about 0.1:10 to 10:0.1 with the other active compounds (2). However, ratios of about 0.5:1.0 to 3.0:1.0 have proved particularly suitable.

The active compound combinations according to the invention not only produce a rapid knock-down action but also bring about the lasting destruction of animal pests, especially insects and arachnids, which occur in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., and Psylla spp.;

from the order of Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmospolites sordidus, Ceuthorrhynchus assimilis, Hypera postica,* Dermestes spp., Trogoderma spp., Anthrenus spp., Attagenus spp., Lyctus spp., *Meligethes aeneus,* Pitnus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarooptes spp., Tarsonemus spp.; *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compounds, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compounds, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides crops protected from damage to arthropods by being grown in areas in which immediately prior to and/or during the time of the growing a composition according to the present invention was applied.

It will be seen that the usual methods of providing a harvested crop may be improved by the present invention.

Ferrocene compounds used in the practice of the invention and their syntheses are shown in the following examples:

EXAMPLE 1

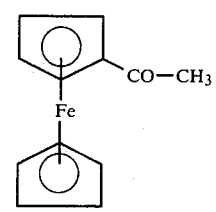
(1)

A mixture of 93.0 g (0.5 mol) of ferrocene, 250 ml of acetic anhydride and 20 ml of 85% strength phosphoric acid was heated to 100° C. for 10 minutes, then cooled and added to ice. After standing overnight, the solid residue was filtered off and washed with water. For further purification, the residue was dissolved in cyclohexane, while warming, animal charcoal/Tonsil being added. The mixture was then filtered and the filtrate was evaporated to dryness under reduced pressure. 64 g (55.4% of theory) of acetylferrocene of melting point 84°–86° C. were obtained in this manner.

The following compounds could be prepared by analogous procedures:

TABLE 1

| Compound No. | Formula | Melting point °C.; boiling point °C. | Yield (% of theory) |
|---|---|---|---|
| 2 | $CO-C_2H_5$ (ferrocenyl) | 132–136/4 mm Hg | 45 |
| 3 | $CO-C_3H_7-n$ (ferrocenyl) | 140/3 mm Hg 35–38 | 49 |
| 4 | $CO-C_4H_9-N$ (ferrocenyl) | 166–170/1 mm Hg | 50 |
| 5 | $CO-(CH_2)_4-CH_3$ (ferrocenyl) | 173–178/1 mm Hg | 48 |
| 6 | $CO(CH_2)_5-CH_3$ (ferrocenyl) | 181–186/1 mm Hg | 59 |
| 7 | $CO(CH_2)_6CH_3$ (ferrocenyl) | 187–190/1 mm Hg | 51 |
| 8 | $CO(CH_2)_7CH_3$ (ferrocenyl) | 190–195/1 mm Hg | 44 39 |

TABLE 1-continued

| Compound No. | Formula | Melting point °C,; boiling point °C. | Yield (% of theory) |
|---|---|---|---|
| 9 | ![](Fe with CO(CH₂)₈CH₃) | 205–210/1 mm Hg 33 | 44 |
| 10 | ![](Fe with two CO—C₆H₅ groups) | 102–3° C. | |
| 11 | ![](Fe with two CO—CH₃ groups) | 125–7° C. | |

EXAMPLE 2

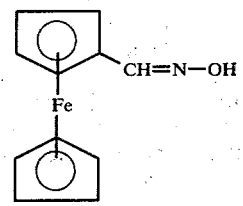
(12)

A solution of 12 g (0.3 mol) of sodium hydroxide in 20 ml of water was added dropwise to a suspension of 20.9 g (0.3 mol) of hydroxylamine hydrochloride in 200 ml of ethanol, while cooling, and a solution of 42.8 g (0.2 mol) of ferrocene-aldehyde in 200 ml of ethanol was then added. After boiling under reflux for 5 hours, the reaction mixture was cooled. The undissolved constituents were filtered off, the filtrate was evaporated to dryness and the residue was suspended in water, filtered off and dried. 42 g (91.7% of theory) of ferrocene-aldoxime of melting point 228° C. were obtained in this manner.

The compounds listed below were prepared by customary reactions, starting from ferrocene-oximes:

TABLE 2

| Compound No. | Formula |
|---|---|
| 13 | ![](Fe with C(CH₃)=N—OC₂H₅) |
| 14 | ![](Fe with CH=N—OCH₃) |

EXAMPLE 3

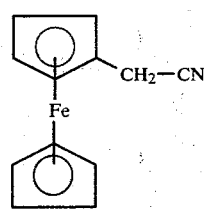
(15)

58 g (0.15 mol) of N,N-dimethylamino-methylferrocene methoiodide were added to a solution of 57 g (0.88 mol) of potassium cyanide in 570 ml of water and the mixture was heated to the boil, the solid material dissolving. Within a few minutes, the evolution of trimethylamine started, while at the same time a volatile oil separated out. After stirring for two hours under reflux, the mixture was cooled to room temperature, whereupon the oily product solidified. The solid material was separated off and the solution which remained was extracted with ether. The combined organic phases were washed with water and, after drying over sodium sulphate, were concentrated under reduced pressure. The residue was recrystallized from 200 ml of hexane. 26 g (76.9% of theory) of cyanomethylferrocene of melting point 82° to 83° C. were obtained in this manner.

EXAMPLE 4

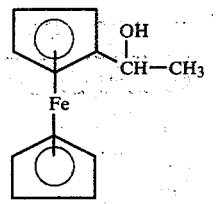
(16)

A solution of 46.2 g (0.2 mol) of acetylferrocene in 200 ml of ethanol was added dropwise, at room temperature, to a solution of 30.4 g (0.8 mol) of sodium borohydride in 200 ml of water. The reaction mixture was stirred overnight at room temperature poured into water and the solid material which was obtained was filtered off. The product was washed and dried. 40 g of 1-hydroxyethylferrocene of melting point 69° C. were obtained in this manner.

The following compound was prepared analogously:

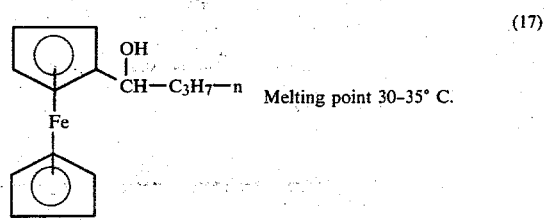
(17) Melting point 30–35° C.

EXAMPLE 5

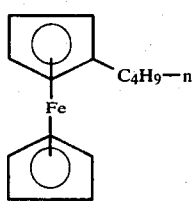 C4H9—n n-Butylferrocene was prepared by reducing n-butyrolferrocene. Boiling point: 130° C./2–3 mm Hg.

The following compounds could be prepared analogously:

TABLE 3

| Compound No. | Formula |
|---|---|
| 19 | Fe—(CH₂)₄CH₃ (ferrocene with n-pentyl) |
| 20 | Fe with two C₄H₉—n substituents |
| Compound 21 Ferrocene-aldehyde | Fe—CHO |
| Compound 22 Ferrocene | 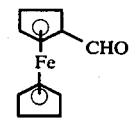 |

The pesticidal activity of the compositions according to this invention is illustrated by the following biotest examples.

EXAMPLE 6

$LT_{100}$ test

Test insects: *Musca domestica* (Weymanns strain), resistant to phosphoric acid esters Solvent: Acetone Solutions were prepared from the active compounds, synergistic agents and mixtures of active compounds and synergistic agents, and 2.5 ml of each solution were pipetted onto a filter paper disc of 9.5 cm diameter in a respective Petri dish. The filter paper absorbed the solution. The Petri dishes were left standing open until were then introduced into each Petri dish, and the dishes were each covered with a glass lid.

The condition of the test insects was checked continuously for up to 6 hours. The time required for a 100% knock down action was determined. If the $LT_{100}$ was not reached after 6 hours, the percentage of the test insects which had been knocked down was determined.

The concentration of the active compounds, synergistic agents and mixtures, and their actions, can be seen from the tables which follow.

TABLE 4

LT 100 test with *Musca domestica* (Weymanns strain) resistant to phosphoric acid esters

| Active compounds ( ) code letter/synergistic agents | Concentrations in % | LT 100 after minutes |
|---|---|---|
| (A) phenyl with —O—C(=O)—NHCH₃ and —OC₃H₇i | 1.0 | 360' = 0% |
| (B) benzofuran derivative with —O—C(=O)—NHCH₃ and gem-dimethyl | 1.0 | 360' = 20% |
| (C) indane derivative with —O—C(=O)—NHCH₃ and CH₃ | 1.0 | 360' = 0% |
| (D) CH₃—NH—C(=O)—O—N=C(CH₃)—S—CH₃ | 0.04 | 360' = 35% |

| Active compounds/synergistic agents | Concentrations in % | LT 100 after minutes |
|---|---|---|

TABLE 4-continued

**LT 100 test with *Musca domestica* (Weymanns strain) resistant to phosphoric acid esters**

| Compound | Dose | Result |
|---|---|---|
| Pyrethrinsas a 25% strength extract | 0.04 | 360' = 0% |
| (E) [cyclopropane carboxylate ester with furan-benzyl] | 0.04 | 360' = 60% |
| (F) | | |
| (G) [α-cyano-3-(4-fluorophenoxy)benzyl 2-(4-chlorophenyl)-3-methylbutyrate] | 1.0 | 120' |
| (H) [3,4-dichloro-α-(trichloromethyl)benzyl acetate] | 1.0 | 360' = 0% |
| (J) [tricyclohexyltin triazole] | 0.2 | 360' = 10% |
| (K) [hexachlorocyclohexane] | 1.0 | 240' |
| (L) [methoxychlor: bis(4-methoxyphenyl)-trichloromethylmethane] | 1.0 | 360' = 50% |
| (M) $NO_2-C_6H_4-O-P(=S)(OC_2H_5)_2$ | 1.0 | 360' = 90% |
| (N) $CH_3-S-C_6H_3(CH_3)-O-P(=S)(OCH_3)_2$ | 1.0 | 360' = 95% |
| (O) $NO_2-C_6H_3(CH_3)-O-P(=S)(OCH_3)_2$ | 0.2 | 360' = 0% |

TABLE 4-continued
LT 100 test with *Musca domestica* (Weymanns strain) resistant to phosphoric acid esters

| Structure (code) | Concentration in % | LT 100 after minutes |
|---|---|---|
| (P) 2,4-Cl$_2$-C$_6$H$_3$-O-P(=S)(OC$_2$H$_5$)(SC$_3$H$_7$n) | 0.2 | 360′ |
| (Q) benzoyl-N(-CH$_2$-S-P(=S)(OCH$_3$)$_2$)-N=N-(benzo fused) | 1.0 | 360′ = 25% |
| (R) CH$_3$S-C$_6$H$_4$-O-P(=S)(OC$_2$H$_5$)(SC$_3$H$_7$n) | 0.2 | 360′ = 50% |
| (S) pyrimidinyl-O-P(=S)(OCH$_3$)(CH$_3$) with CH$_3$-O and isopropyl substituents | 0.008 | 240′ |
| (T) 2-isopropyl-4-methyl-pyrimidin-6-yl-O-P(=S)(OC$_2$H$_5$)$_2$ | 1.0 | 150′ |
| (U) 3-chloro-4-methylcoumarin-7-yl-O-P(=S)(OC$_2$H$_5$)$_2$ | 1.0 | 360′ = 0% |
| (V) CCl$_3$-CH(OH)-P(=O)(OCH$_3$)$_2$ | 0.2 | 360′ = 35% |

| Active compounds or synergistic agent ( ) code letter    ( ) Example No. | Concentrations in % | LT 100 after minutes |
|---|---|---|
| CCl$_2$=CH-O-P(=O)(OCH$_3$)$_2$ (W) | 0.04 | 210′ |
| CH$_3$-NH-C(=O)-CH$_2$-S-P(=O)(OCH$_3$)$_2$ (X) | 0.2 | 360′ = 95% |
| C$_6$H$_4$(-O-C(=O)-NHCH$_3$)(-CH$_2$-S-C$_2$H$_5$) (Y) | 1.0 | 360′ = 0% |
| methylenedioxyphenyl-CH$_2$OCH$_2$-CH$_2$-O-CH$_2$-CH$_2$-O-C$_4$H$_9$ / -CH$_2$-CH$_2$-CH$_3$ | 1.0 | 360′ = 0% |

TABLE 4-continued

LT 100 test with *Musca domestica* (Weymanns strain) resistant to phosphoric acid esters

| Compound | | Dose | Result |
|---|---|---|---|
| 1 | 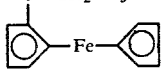 O=C—CH$_2$CH$_3$ / Fe | 1.0 | 360' = 0% |
| 2 | 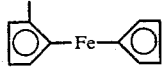 O=C—CH$_2$—CH$_2$—CH$_3$ / Fe | 1.0 | 360' = 0% |
| 3 | 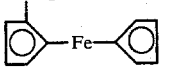 CH$_2$—CH$_2$—CH$_2$—CH$_3$ / Fe | 1.0 | 360' = 35% |
| 18 | 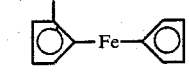 CH$_3$—C=N—OC$_2$H$_5$ / Fe | 1.0 | 360' = 0% |
| 13 | 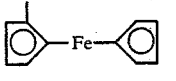 CH=N—OCH$_3$ / Fe | 1.0 | 360' = 0% |
| 14 | 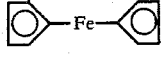 HOCH—CH$_3$ / Fe | 1.0 | 360' = 0% |
| 16 | 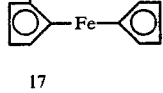 HOCH—CH$_2$—CH$_2$CH$_3$ / Fe | 1.0 | 360' = 0% |
| 17 | 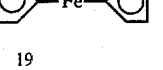 CH$_2$—CH$_2$—CH$_2$—CH$_2$CH$_3$ / Fe | 1.0 | 360' = 0% |
| 19 | 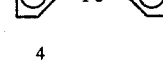 O=C—CH$_2$—CH$_2$—CH$_2$CH$_3$ / Fe | 1.0 | 360' = 0% |
| 4 |  O=C—CH$_2$—CH$_2$—CH$_2$—CH$_2$—CH$_3$ / Fe | 1.0 | 360' = 0% |
| 5 |  O=C—CH$_2$—CH$_2$—CH$_2$—CH$_2$—CH$_2$—CH$_2$—CH$_3$ / Fe | 1.0 | 360' = 0% |
| 7 |  O=C—(CH$_2$)$_7$—CH$_3$ / Fe | 1.0 | 360' = 0% |
| 8 | | | |

TABLE 4-continued

LT 100 test with *Musca domestica* (Weymanns strain) resistant to phosphoric acid esters

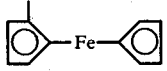
9

| Active compound/synergistic agent | Concentration in % | LT 100 after minutes |
|---|---|---|
| 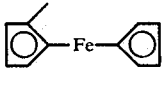 (21) | 1.0 | 360' = 0% |
| 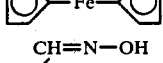 (22) | 1.0 | 360' = 0% |
| 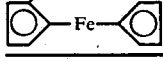 (12) | 1.0 | 360' = 0% |

TABLE 5

LT 100 test with *Musca domestica*, Weymanns strain, resistant to phosphoric acid esters (continuation)

| Active compound (code letter) | + Synergistic agent Compound No. | Concentrations in % Active compound | + Synergistic agent | LT 100 after minutes |
|---|---|---|---|---|
| A | + Piperonyl butoxide | 1.0 | + 1.0 | 360' = 90% |
| A | + 22 | 0.2 | + 0.2 | 150' |
| A | + 2 | 0.2 | + 0.2 | 360' = 90% |
| A | + 3 | 1.0 | + 1.0 | 150' |
| A | + 18 | 0.04 | + 0.04 | 180' |
| A | + 13 | 0.2 | + 0.2 | 360' = 95% |
| A | + 14 | 0.04 | + 0.04 | 360' |
| A | + 16 | 0.2 | + 0.2 | 360' |
| A | + 17 | 0.2 | + 0.2 | 360' |
| B | + Piperonyl butoxide | 1.0 | + 1.0 | 360' = 30% |
| B | + 2 | 0.2 | + 0.2 | 360' = 95% |
| B | + 3 | 0.2 | + 0.2 | 360' = 95% |
| B | + 18 | 0.008 | + 0.008 | 210' |
| B | + 13 | 1.0 | + 1.0 | 360' |
| B | + 14 | 0.04 | + 0.04 | 360' |
| B | + 16 | 0.04 | + 0.04 | 180' |
| B | + 17 | 0.04 | + 0.04 | 360' |
| B | + 19 | 0.04 | + 0.04 | 240' |
| C | + Piperonyl butoxide | 0.2 | + 0.2 | 360' = 40% |
| C | + 22 | 0.04 | + 0.04 | 210' |
| C | + 2 | 0.2 | + 0.2 | 360' |
| C | + 18 | 0.04 | + 0.04 | 90' |
| C | + 14 | 0.2 | + 0.2 | 180' |
| C | + 16 | 0.2 | + 0.2 | 105' |
| C | + 19 | 0.04 | + 0.04 | 150' |
| C | + 4 | 0.2 | + 0.2 | 360' |
| D | + Piperonyl butoxide | 0.04 | + 0.04 | 360' = 90% |
| D | + 22 | 0.04 | + 0.04 | 150' |
| D | + 18 | 0.04 | + 0.04 | 120' |
| D | + 13 | 0.04 | + 0.04 | 180' |
| D | + 14 | 0.04 | + 0.04 | 120' |
| D | + 19 | 0.04 | + 0.04 | 150' |
| E | + 18 | 0.04 | + 0.04 | 240' |
| E | + 14 | 0.04 | + 0.04 | 360' = 90% |
| E | + 17 | 0.04 | + 0.04 | 180' |
| E | + 19 | 0.04 | + 0.04 | 150' |
| F | + Piperonyl butoxide | 0.04 | + 0.04 | 105' |
| F | + 2 | 0.04 | + 0.04 | 90' |
| F | + 3 | 0.04 | + 0.04 | 90' |
| G | + Piperonyl butoxide | 0.2 | + 0.2 | 150' |
| G | + 21 | 0.2 | + 0.2 | 90' |
| G | + 22 | 0.2 | + 0.2 | 90' |
| G | + 3 | 0.2 | + 0.2 | 120' |
| G | + 18 | 0.2 | + 0.2 | 90' |
| G | + 14 | 0.2 | + 0.2 | 120' |
| G | + 16 | 0.2 | + 0.2 | 90' |
| G | + 17 | 0.2 | + 0.2 | 90' |
| G | + 19 | 0.2 | + 0.2 | 120' |
| G | + 9 | 0.2 | + 0.2 | 120' |
| H | + Piperonyl butoxide | 1.0 | + 1.0 | 360' = 40% |

TABLE 5-continued

LT 100 test with *Musca domestica*, Weymanns strain, resistant to phosphoric acid esters (continuation)

| Active compound (code letter) | + Synergistic agent Compound No. | Concentrations in % Active compound | + Synergistic agent | LT 100 after minutes |
|---|---|---|---|---|
| H | + 18 | 1.0 | + 1.0 | 360' |
| H | + 14 | 1.0 | + 1.0 | 360' = 90% |
| H | + 16 | 1.0 | + 1.0 | 360' |
| H | + 17 | 1.0 | + 1.0 | 360' |
| H | + 19 | 1.0 | + 1.0 | 360' |
| J | + Piperonyl butoxide | 0.2 | + 0.2 | 360' = 25% |
| J | + 14 | 0.2 | + 0.2 | 360' = 80% |
| K | + Piperonyl butoxide | 1.0 | + 1.0 | 180' |
| K | + 21 | 1.0 | + 1.0 | 120' |
| K | + 22 | 1.0 | + 1.0 | 150' |
| K | + 12 | 1.0 | + 1.0 | 120' |
| K | + 2 | 1.0 | + 1.0 | 150' |
| K | + 3 | 1.0 | + 1.0 | 150' |
| K | + 18 | 0.2 | + 0.2 | 120' |
| K | + 14 | 0.2 | + 0.2 | 105' |
| K | + 16 | 0.2 | + 0.2 | 150' |
| K | + 17 | 0.2 | + 0.2 | 150' |
| K | + 19 | 0.2 | + 0.2 | 150' |
| K | + 4 | 0.2 | + 0.2 | 150' |
| K | + 5 | 0.2 | + 0.2 | 150' |
| K | + 7 | 0.2 | + 0.2 | 150' |
| K | + 8 | 1.0 | + 1.0 | 150' |
| K | + 9 | 1.0 | + 1.0 | 105' |
| L | + Piperonyl butoxide | 1.0 | + 1.0 | 6 hrs = 95% |
| L | + 21 | 1.0 | + 1.0 | 105' |
| L | + 18 | 0.2 | + 0.2 | 150' |
| L | + 14 | 0.2 | + 0.2 | 150' |
| L | + 16 | 0.2 | + 0.2 | 210' |
| L | + 19 | 0.2 | + 0.2 | 6 hrs = 95% |
| M | + Piperonyl butoxide | 1.0 | + 1.0 | 6 hrs = 95% |
| M | + 22 | 0.2 | + 0.2 | 180' |
| M | + 3 | 1.0 | + 1.0 | 180' |
| M | + 18 | 0.2 | + 0.2 | 210' |
| M | + 13 | 1.0 | + 1.0 | 210' |
| M | + 14 | 1.0 | + 1.0 | 180' |
| M | + 19 | 1.0 | + 1.0 | 180' |
| M | + 4 | 1.0 | + 1.0 | 180' |
| M | + 5 | 1.0 | + 1.0 | 210' |
| M | + 8 | 1.0 | + 1.0 | 210' |
| N | + Piperonyl butoxide | 1.0 | + 1.0 | 360' |
| N | + 3 | 1.0 | + 1.0 | 180' |
| N | + 19 | 1.0 | + 1.0 | 210' |
| O | + Piperonyl butoxide | 0.2 | + 0.2 | 360' = 55% |
| O | + 22 | 0.2 | + 0.2 | 360' |
| O | + 18 | 0.2 | + 0.2 | 360' |
| O | + 14 | 0.2 | + 0.2 | 360' |
| O | + 16 | 0.2 | + 0.2 | 360' |
| O | + 19 | 0.2 | + 0.2 | 360' |
| P | + Piperonyl butoxide | 0.2 | + 0.2 | 360' = 75% |
| P | + 22 | 0.2 | + 0.2 | 240' |
| P | + 3 | 0.2 | + 0.2 | 240' |
| P | + 18 | 0.2 | + 0.2 | 210' |
| P | + 14 | 0.2 | + 0.2 | 240' |
| P | + 5 | 0.2 | + 0.2 | 240' |
| Q | + Piperonyl butoxide | 1.0 | + 1.0 | 360' = 55% |
| Q | + 22 | 1.0 | + 1.0 | 240' |
| Q | + 18 | 0.2 | + 0.2 | 180' |
| Q | + 14 | 0.2 | + 0.2 | 210' |
| Q | + 16 | 1.0 | + 1.0 | 210' |
| Q | + 17 | 1.0 | + 1.0 | 210' |
| Q | + 19 | 1.0 | + 1.0 | 210' |
| Q | + 4 | 1.0 | + 1.0 | 180' |
| R | + Piperonyl butoxide | 0.2 | + 0.2 | 360' |
| R | + 14 | 0.2 | + 0.2 | 210' |
| R | + 19 | 0.2 | + 0.2 | 240' |
| R | + 4 | 0.2 | + 0.2 | 240' |
| R | + 8 | 0.2 | + 0.2 | 240' |
| R | + 9 | 0.2 | + 0.2 | 240' |
| S | + Piperonyl butoxide | 0.008 | + 0.008 | 240' |
| S | + 21 | 0.008 | + 0.008 | 210' |
| S | + 22 | 0.008 | + 0.008 | 180' |
| S | + 12 | 0.008 | + 0.008 | 180' |
| S | + 2 | 0.008 | + 0.008 | 150' |
| S | + 3 | 0.008 | + 0.008 | 150' |
| S | + 18 | 0.0016 | + 0.0016 | 210' |
| S | + 13 | 0.008 | + 0.008 | 150' |

TABLE 5-continued

LT 100 test with *Musca domestica*, Weymanns strain, resistant to phosphoric acid esters (continuation)

| Active compound (code letter) | + Synergistic agent Compound No. | Concentrations in % Active compound | + Synergistic agent | LT 100 after minutes |
|---|---|---|---|---|
| S | + 14 | 0.008 | + 0.008 | 120' |
| S | + 16 | 0.008 | + 0.008 | 150' |
| S | + 17 | 0.008 | + 0.008 | 120' |
| S | + 19 | 0.008 | + 0.008 | 150' |
| S | + 4 | 0.008 | + 0.008 | 120' |
| S | + 5 | 0.008 | + 0.008 | 210' |
| S | + 7 | 0.008 | + 0.008 | 210' |
| T | + Piperonyl butoxide | 1.0 | + 1.0 | 210' |
| T | + 21 | 0.2 | + 0.2 | 150' |
| T | + 22 | 0.2 | + 0.2 | 150' |
| T | + 12 | 1.0 | + 1.0 | 180' |
| T | + 2 | 0.2 | + 0.2 | 180' |
| T | + 3 | 1.0 | + 1.0 | 105' |
| T | + 18 | 0.2 | + 0.2 | 105' |
| T | + 13 | 1.0 | + 1.0 | 120' |
| T | + 14 | 0.2 | + 0.2 | 105' |
| T | + 16 | 0.02 | + 0.2 | 150' |
| T | + 17 | 0.2 | + 0.2 | 150' |
| T | + 19 | 0.2 | + 0.2 | 120' |
| T | + 4 | 0.2 | + 0.2 | 120' |
| U | + Piperonyl butoxide | 1.0 | + 1.0 | 360' = 0% |
| U | + 18 | 0.2 | + 0.2 | 240' |
| U | + 13 | 0.2 | + 0.2 | 360' = 95% |
| U | + 14 | 0.04 | + 0.04 | 360' |
| U | + 16 | 0.2 | + 0.2 | 360' = 95% |
| U | + 17 | 1.0 | + 1.0 | 360' = 95% |
| U | + 19 | 1.0 | + 1.0 | 360' = 95% |
| V | + Piperonyl butoxide | 0.2 | + 0.2 | 360' = 35% |
| V | + 21 | 0.2 | + 0.2 | 360' |
| V | + 22 | 0.2 | + 0.2 | 120' |
| V | + 12 | 0.04 | + 0.04 | 360' = 65% |
| V | + 2 | 0.2 | + 0.2 | 360' |
| V | + 3 | 0.2 | + 0.2 | 360' |
| V | + 18 | 0.2 | + 0.2 | 75' |
| V | + 13 | 0.2 | + 0.2 | 180' |
| V | + 14 | 0.2 | + 0.2 | 180' |
| V | + 16 | 0.04 | + 0.04 | 360' |
| V | + 17 | 0.04 | + 0.04 | 360' |
| V | + 19 | 0.04 | + 0.04 | 240' |
| V | + 4 | 0.04 | + 0.04 | 360' = 95% |
| V | + 5 | 0.04 | + 0.04 | 360' = 95% |
| V | + 8 | 0.04 | + 0.04 | 360' = 90% |
| W | + Piperonyl butoxide | 0.04 | + 0.04 | 360' = 95% |
| W | + 21 | 0.04 | + 0.04 | 90' |
| W | + 2 | 0.04 | + 0.04 | 120' |
| W | + 3 | 0.04 | + 0.04 | 150' |
| W | + 18 | 0.04 | + 0.04 | 90' |
| W | + 13 | 0.04 | + 0.04 | 180' |
| W | + 14 | 0.04 | + 0.04 | 105' |
| W | + 17 | 0.04 | + 0.04 | 90' |
| W | + 19 | 0.04 | + 0.04 | 90' |
| W | + 4 | 0.04 | + 0.04 | 150' |
| W | + 5 | 0.04 | + 0.04 | 180' |
| W | + 9 | 0.04 | + 0.04 | 180' |
| X | + Piperonyl butoxide | 0.2 | + 0.2 | 360' |
| X | + 21 | 0.2 | + 0.02 | 120' |
| X | + 22 | 0.2 | + 0.2 | 90' |
| X | + 12 | 0.2 | + 0.2 | 180' |
| X | + 2 | 0.2 | + 0.2 | 150' |
| X | + 3 | 0.2 | + 0.2 | 210' |
| X | + 18 | 0.04 | + 0.04 | 180' |
| X | + 14 | 0.04 | + 0.04 | 210' |
| X | + 16 | 0.2 | + 0.2 | 120' |
| X | + 17 | 0.2 | + 0.2 | 105' |
| X | + 19 | 0.2 | + 0.2 | 90' |
| X | + 4 | 0.2 | + 0.2 | 210' |
| X | + 5 | 0.2 | + 0.2 | 150' |
| X | + 7 | 0.2 | + 0.2 | 150' |
| X | + 8 | 0.2 | + 0.2 | 150' |
| X | + 9 | 0.2 | + 0.2 | 90' |
| A | + Piperonylbutoxide | 0.2 | + 0.1 | 360' = 10% |
|  |  | 0.2 | + 0.2 | 360' = 60% |
|  |  | 0.2 | + 0.4 | 360' = 70% |
|  |  | 0.2 | + 1.0 | 210' |
| A | + 22 | 0.2 | + 0.1 | 120' |
|  |  | 0.2 | + 0.2 | 150' |

TABLE 5-continued

LT 100 test with *Musca domestica*, Weymanns strain, resistant to phosphoric acid esters (continuation)

| Active compound (code letter) | + Synergistic agent Compound No. | Active compound | + Synergistic agent | LT 100 after minutes |
|---|---|---|---|---|
| | | 0.2 | + 0.4 | 105' |
| | | 0.2 | + 1.0 | 105' |
| A | + 18 | 0.2 | + 0.1 | 75' |
| | | 0.2 | + 0.2 | 75' |
| | | 0.2 | + 0.4 | 60' |
| | | 0.2 | + 1.0 | 45' |
| A | + 14 | 0.2 | + 0.1 | 150' |
| | | 0.2 | + 0.2 | 150' |
| | | 0.2 | + 0.4 | 120' |
| | | 0.2 | + 1.0 | 60' |
| A | + 16 | 0.2 | + 0.1 | 210' |
| | | 0.2 | + 0.2 | 75' |
| | | 0.2 | + 0.4 | 75' |
| | | 0.2 | + 1.0 | 75' |

EXAMPLE 7

LT$_{100}$ test
Test insects: *Blattella germanica* ♀ *Tribolium confusum*
Solvent: Acetone Solutions were prepared from the active compounds, synergistic agents and mixtures of active compounds and synergistic agents, and 2.5 ml of each solution were pipetted onto a filterpaper of 9.5 cm diameter in a respective Petri dish. The filterpaper absorbed the solution. The Petri dishes were left standing open until the solvent had completely evaporated. 25 test insects were then introduced into each Petri dish, and the dish was covered with a glass lid.

The condition of the insects was checked continuously for up to 6 hours and thereafter again after 24, 48 and 72 hours. The time required for a 100% knock down action was determined. If the LT$_{100}$ was not reached after 72 hours, the percentage of the test insects which had been knocked down was determined.

The concentrations of the active compounds, synergistic agents and mixtures, and their actions, can be seen from the table which follows.

TABLE 6

LT$_{100}$ test with various pests

| Active compound Code letter | + Synergistic agent Compound No. | Pest | Active compound | + | Synergistic agent | LT 100 after minutes or hours |
|---|---|---|---|---|---|---|
| A | | *Blattella germ.* ♀♀ | 0.008 | | | 72 hrs = 80% |
| | Piperonyl butoxide | " | | | 1.0 | 72 hrs = 20% |
| A | + Piperonyl butoxide | " | 0.008 | + | 0.008 | 180' |
| | 3 | " | | | 0.2 | 72 hrs |
| A | + 3 | " | 0.008 | + | 0.008 | 150' |
| | 18 | " | | | 0.2 | 72 hrs = 80% |
| A | + 18 | " | 0.008 | + | 0.008 | 150' |
| | 14 | " | | | 0.2 | 72 hrs = 80% |
| A | + 14 | " | 0.008 | + | 0.008 | 105' |
| | 16 | " | | | 0.2 | 72 hrs |
| A | + 16 | " | 0.008 | + | 0.008 | 150' |
| | 17 | " | | | 0.2 | 72 hrs |
| A | + 17 | " | 0.008 | + | 0.008 | 150' |
| B | | *Blattella germ.* ♀♀ | 0.008 | | | 72 hrs = 20% |
| B | + Piperonyl butoxide | " | 0.008 | + | 0.008 | 72 hrs = 40% |
| | 2 | " | | | 0.008 | 72 hrs = 20% |
| B | + 2 | " | 0.008 | + | 0.008 | 150' |
| B | + 14 | " | 0.008 | + | 0.008 | 150' |
| Y | | *Blattella germ.* ♀♀ | 0.04 | | | 72 hrs = 0% |
| Y | + Piperonyl butoxide | " | 0.04 | + | 0.04 | 72 hrs = 0% |
| Y | + 2 | " | 0.04 | + | 0.04 | 24 hrs |
| Y | + 3 | " | 0.04 | + | 0.04 | 72 hrs = 80% |
| Y | + 18 | " | 0.04 | + | 0.04 | 240' |
| Y | + 14 | " | 0.04 | + | 0.04 | 72 hrs = 80% |
| Y | + 16 | " | 0.04 | + | 0.04 | 72 hrs = 80% |
| Y | + 19 | " | 0.04 | + | 0.04 | 24 hrs |
| F | | *Blattella germ.* ♀♀ | 0.008 | | | 72 hrs = 80% |
| F | + Piperonyl butoxide | " | 0.008 | + | 0.008 | 24 hrs |
| F | + 2 | " | 0.008 | + | 0.008 | 120' |
| F | + 18 | " | 0.008 | + | 0.008 | 210' |
| F | + 17 | " | 0.008 | + | 0.008 | 360' |
| E | | *Blattella germ.* ♀♀ | 0.04 | | | 24 hrs |
| E | + 2 | " | 0.04 | + | 0.04 | 180' |
| E | + 3 | " | 0.04 | + | 0.04 | 90' |
| E | + 18 | " | 0.04 | + | 0.04 | 105' |
| E | + 14 | " | 0.008 | + | 0.008 | 90' |
| E | + 16 | " | 0.04 | + | 0.04 | 150' |
| E | + 17 | " | 0.04 | + | 0.04 | 30' |
| E | + 19 | " | 0.04 | + | 0.04 | 180' |

TABLE 6-continued
LT₁₀₀ test with various pests

| Active compound Code letter | + Synergistic agent Compound No. | Pest | Active compound | + | Synergistic agent | LT 100 after minutes or hours |
|---|---|---|---|---|---|---|
| H | | *Blattella germ.* ♀ ♀ | 1.0 | | | 72 hrs = 20% |
| H | + Piperonyl butoxide | " | 1.0 | + | 1.0 | 72 hrs = 0% |
| H | + 2 | " | 0.2 | + | 0.2 | 72 hrs |
| H | + 3 | " | 0.2 | + | 0.2 | 72 hrs |
| H | + 18 | " | 0.2 | + | 0.2 | 72 hrs |
| H | + 14 | " | 0.2 | + | 0.2 | 72 hrs |
| H | + 16 | " | 0.2 | + | 0.2 | 72 hrs |
| H | + 17 | " | 0.2 | + | 0.2 | 72 hrs |
| N | | *Blattella germ.* ♀ ♀ | 0.2 | | | 360' |
| N | + Piperonyl butoxide | " | 0.2 | + | 0.2 | 24 hrs |
| N | + 2 | " | 0.2 | + | 0.2 | 210' |
| N | + 3 | " | 0.2 | + | 0.2 | 180' |
| N | + 18 | " | 0.2 | + | 0.2 | 180' |
| N | + 13 | " | 0.04 | + | 0.04 | 210' |
| N | + 14 | " | 0.2 | + | 0.2 | 180' |
| N | + 16 | " | 0.2 | + | 0.2 | 180' |
| N | + 17 | " | 0.2 | + | 0.2 | 180' |
| N | + 19 | " | 0.2 | + | 0.2 | 180' |
| A | | *Tribolium confusum* | 0.04 | | | 72 hrs = 80% |
| A | Piperonyl butoxide | " | | | 1.0 | 72 hrs = 0% |
| A | + Piperonyl butoxide | " | 0.04 | + | 0.04 | 72 hrs = 80% |
| A | + 2 | " | 0.04 | + | 0.04 | 24 hrs |
| A | + 3 | " | 0.04 | + | 0.04 | 180' |
| A | + 18 | " | 0.04 | + | 0.04 | 90' |
| A | + 14 | " | 0.04 | + | 0.04 | 180' |
| A | + 19 | " | 0.04 | + | 0.04 | 180' |
| B | | *Tribolium confusum* | 0.04 | | | 120' |
| B | + Piperonyl butoxide | " | 0.04 | + | 0.04 | 105' |
| B | + 2 | " | 0.04 | + | 0.04 | 75' |
| B | + 3 | " | 0.04 | + | 0.04 | 90' |
| B | + 18 | " | 0.04 | + | 0.04 | 45' |
| B | + 14 | " | 0.04 | + | 0.04 | 60' |
| B | + 16 | " | 0.04 | + | 0.04 | 45' |
| B | + 17 | " | 0.04 | + | 0.04 | 45' |
| B | + 19 | " | 0.04 | + | 0.04 | 45' |
| Y | | *Tribolium confusum* | 1.0 | | | 72 hrs = 0% |
| Y | + Piperonyl butoxide | " | 1.0 | + | 1.0 | 72 hrs = 10% |
| Y | + 18 | " | 0.2 | + | 0.2 | 24 hrs |
| Y | + 19 | " | 0.2 | + | 0.2 | 72 hrs |
| F | | *Tribolium confusum* | 0.2 | | | 45' |
| F | + Piperonyl butoxide | " | 0.2 | + | 0.2 | 45' |
| F | + 2 | " | 0.2 | + | 0.2 | 30' |
| F | + 13 | " | 0.2 | + | 0.2 | 30' |
| F | + 14 | " | 0.2 | + | 0.2 | 30' |
| H | | *Tribolium confusum* | 1.0 | | | 72 hrs = 0% |
| H | + Piperonyl butoxide | " | 1.0 | + | 1.0 | 72 hrs = 0% |
| H | + 18 | " | 1.0 | + | 1.0 | 72 hrs |
| H | + 14 | " | 1.0 | + | 1.0 | 72 hrs |
| H | + 16 | " | 1.0 | + | 1.0 | 72 hrs |
| H | + 17 | " | 1.0 | + | 1.0 | 72 hrs |

It will be appreciated that the instant specification and examples are set forth by way of illustration and not limitation, and that various modification and changes may be made without departing from the spirit and scope of the present invention.

What we claim is:

1. An arthropodicidal composition containing, as active ingredient, an arthropodicidally effective amount of (1) at least one ferrocene derivative of the formula

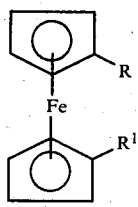

in which

R and $R^1$ each independently is hydrogen, alkyl, or alkenyl with up to 20 carbon atoms, alkyl or alkenyl with up to 10 carbon atoms substituted by carbalkoxy with up to 4 carbon atoms per alkoxy, benzyl, nitrile, cyanomethyl, cyanoethyl;

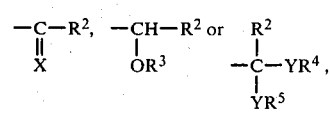

$R^2$ is hydrogen, alkoxy with 1 to 10 carbon atoms; alkyl with 1 to 19 carbon atoms, cycloalkyl with 3 to 12 carbon atoms or phenyl optionally carrying at least one halogen, alkyl, hydroxyl, halogenoalkyl, nitro, nitrile or alkoxy substituent, $R^3$ is hydrogen or alkyl with 1 to 8 carbon atoms, $R^4$ and $R^5$ each independently is alkyl with 1 to 6 carbon atoms or together are an alkylene radical with 1 to 6 carbon atoms, X is oxygen, hydroxyimino or alkoxyimino with 1 to 6 carbon atoms, and Y is oxygen or sulphur, and (2) a compound selected from the group consisting of (A) carboxylic acid esters of the formula $$R^{11}-CO-O-\overset{R^{12}}{\underset{|}{CH}}-R^{13}$$

in which

R$^{11}$ is alkyl with 1 to 6 carbon atoms optionally substituted by phenyl or halophenyl; phenyl; halophenyl; or cyclopropyl optionally substituted by alkyl, alkenyl, halogenoalkyl or halogenoalkenyl each with up to 6 carbon atoms, R$^{12}$ is hydrogen, alkyl with 1 to 6 carbon atoms, halogenoalkyl with 1 to 4 carbon atoms and up to 3 halogen atoms, alkenyl, ethynyl or nitrile, and R$^{13}$ is phenyl optionally substituted by C$_{1-4}$-alkyl, halogen, phenoxy, halophenoxy, methyl-phenoxy or benzyl; furanyl, tetrahydrophthalimido or benzodioxolyl any of which is optionally substituted by halogen, alkyl or alkenyl with up to 4 carbon atoms or benzyl or, together with R$^{12}$, forms a cyclopentenone ring which is optionally substituted by C$_{1-4}$-alkyl, furfuryl or C$_{1-5}$-alkenyl, and naturally occurring pyrethroids, and (B) phosphoric acid esters of the formula $$R^{14}-X'-\overset{\overset{X'}{\underset{\|}{}}\,X'-R^{15}}{\underset{Y'-R^{16}}{P}}$$

in which

X' each independently is O or S,

Y' is O, S, —NH— or a direct bond between the central P atom and the radical R$^{16}$, R$^{14}$ and R$^{15}$ each independently is C$_{1-4}$-alkyl or phenyl, and R$^{16}$ is alkyl with 1 to 4 carbon atoms which is optionally substituted by halogen, hydroxyl, nitrile, optionally halogen-substituted phenyl, carbonylamide, sulphonylalkyl, sulphoxyalkyl, carbonylalkyl, alkoxy, alkylmercapto or alkoxycarbonyl; alkenyl with up to 4 carbon atoms which is optionally substituted by halogen, optionally halogen-substituted phenyl or alkoxycarbonyl; aralkyl; phenyl which is optionally substituted by methyl, nitro, nitrile, halogen or methylthio; a pyridine, quinoline, quinoxaline, pyrimidine, diazinone or benzo-1,3,4-triazine radical which is optionally substituted by C$_{1-4}$-alkyl or halogen; dioxanyl; an oxime radical; or a radical identical to that to which it is bonded, the weight ratio of component (1) to component (2) being from about 0.1:10 to 10:0.1.

2. A composition according to claim 1, in which the weight ratio of component (1) to component (2) is from about 0.5:1 to 3:1, the composition containing from about 5 to 99.9% by weight of a diluent.

3. A composition according to claim 1, wherein component (1) is butyrylferrocene.

4. A composition according to claim 1, wherein component (1) is valerylferrocene.

5. A composition according to claim 1, wherein component (1) is 1-hydroxyethylferrocene.

6. A composition according to claim 1, wherein component (1) is n-butylferrocene.

7. A composition according to claim 1, wherein component (1) is n-pentylferrocene.

8. A method of combating arthropods which comprises applying to the arthropods, or to a habitat thereof, an arthropodicidally effective amount of a composition according to claim 1.

9. A method of combating arthropods which comprises applying to the arthropods, or to a habitat thereof, an arthropodically effective amount of a composition according to claim 1 in which component (1) is selected from the group consisting of
butyrylferrocene,
valerylferrocene,
1-hydroxyethylferrocene
n-butylferrocene, and
n-pentylferrocene.

10. A composition according to claim 1, wherein component (2) is (A).

* * * * *